(12) United States Patent
Bagozzi et al.

(10) Patent No.: US 8,292,174 B2
(45) Date of Patent: Oct. 23, 2012

(54) MEDICAL DEVICE TRACKING SYSTEM WITH CAPSULE AND METHOD

(75) Inventors: Christopher A. Bagozzi, Memphis, TN (US); Thor M Hanna, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 7 days.

(21) Appl. No.: 13/006,574

(22) Filed: Jan. 14, 2011

(65) Prior Publication Data

US 2011/0114514 A1   May 19, 2011

Related U.S. Application Data

(62) Division of application No. 12/109,534, filed on Apr. 25, 2008, now Pat. No. 7,909,249.

(51) Int. Cl.
*G06F 19/00* (2011.01)
(52) U.S. Cl. .................. 235/385; 235/375; 705/28
(58) Field of Classification Search .............. 235/375, 235/385; 705/28
See application file for complete search history.

(56) References Cited

U.S. PATENT DOCUMENTS

| | | | |
|---|---|---|---|
| 4,154,342 A | 5/1979 | Wallace | |
| 4,553,669 A | 11/1985 | Butterworth et al. | |
| 4,856,648 A | 8/1989 | Krueger | |
| 7,118,029 B2 | 10/2006 | Nycz et al. | |
| 7,213,767 B2 | 5/2007 | Tethrake et al. | |
| 7,256,699 B2 | 8/2007 | Tethrake et al. | |
| 7,268,684 B2 | 9/2007 | Tethrake et al. | |
| 7,362,228 B2 | 4/2008 | Nycz et al. | |
| 2002/0004660 A1 | 1/2002 | Henniges et al. | |
| 2005/0033430 A1 | 2/2005 | Powers et al. | |
| 2006/0244652 A1 | 11/2006 | Tethrake et al. | |
| 2007/0001839 A1 | 1/2007 | Cambre et al. | |
| 2007/0095689 A1 | 5/2007 | Pratt et al. | |
| 2007/0125392 A1 | 6/2007 | Olson et al. | |
| 2007/0144926 A1 | 6/2007 | Bettenhausen et al. | |
| 2007/0159337 A1 | 7/2007 | Tethrake et al. | |
| 2007/0188306 A1 | 8/2007 | Tethrake et al. | |
| 2007/0239289 A1 | 10/2007 | Cambre et al. | |
| 2007/0284428 A1 | 12/2007 | Cambre et al. | |
| 2008/0230421 A1 | 9/2008 | Pleil et al. | |
| 2008/0230422 A1 | 9/2008 | Pleil et al. | |
| 2008/0230423 A1 | 9/2008 | Loeffler et al. | |

FOREIGN PATENT DOCUMENTS

| | | |
|---|---|---|
| DE | 202007004638 | 6/2007 |
| EP | 1842505 | 10/2007 |
| JP | 2008052013 | 3/2008 |
| WO | 2006124188 | 11/2006 |
| WO | WO 2006124188 A2 * | 11/2006 |

* cited by examiner

*Primary Examiner* — Michael G Lee
*Assistant Examiner* — Matthew Mikels

(57) ABSTRACT

Embodiments of the invention include systems and methods for tracking a medical device. Systems configured for such tracking may include the capability to either or both detect tampering with the medical device and to effectively expose an encapsulated medical device to sterilization substances and associate the medical device with an identifying characteristic.

12 Claims, 6 Drawing Sheets

MEDICAL DEVICE TRACKING SYSTEM WITH CAPSULE AND METHOD

CROSS-REFERENCE TO RELATED APPLICATONS

This application claims priority to and is a divisional of U.S. patent application Ser. No. 12/109,534 filed on Apr. 25, 2008, which is hereby incorporated herein by reference in its entirety.

FIELD OF THE INVENTION

The present invention relates generally to the field of identification and tracking of parts, and more particularly relates to associating a medical device with identifying information provided as part of a capsule in which the medical device is placed, and tracking the medical device.

BACKGROUND

Implantable medical devices must be sterile prior to use in order to reduce the risk of infection in patients receiving such devices. Generally, there are two ways to provide sterile surgical devices. One way is to sterilize a device to be implanted immediately prior to implantation. Another way is to sterilize a device during the manufacturing process, and then to ship the device to a user in a sterilized condition. The first way is typically called providing a device "non-sterile," because the manufacturer ships the device in a condition that is not adequately sterilized for implantation. The second way is typically called providing a device "sterile," because the device is ready for implantation when shipped from the manufacturer.

There is a strong and growing need to track medical devices from their base materials and manufacture to their use, and throughout the intervening time. Tracking of medical devices may also be referred to as maintaining traceability of the devices. It is sometimes important to track medical devices so that patients can be notified of any information related to the safety or longevity of devices once implanted. The U.S. Food and Drug Administration is currently considering requiring that implantable medical devices be uniquely identified and tracked through the time of use of the devices.

It is relatively straightforward to uniquely identify and track sterile medical devices. Unique labels or other indicia are applied to the product and the labels or other indicia remain associated with the medical device until the device is used. In some instances, sterile product labels include adhesive portions that can be applied to a chart or file of a patient to conveniently associate the sterile medical device with a particular patient.

Non-sterile products provide a greater tracking challenge, although there are several reasons for preferring non-sterile shipment of medical devices. A larger number of non-sterile devices can be provided in groups or sets that present the devices in a manner where the devices are readily available for use. The large number of devices may represent a large number of sizes and optional configurations that provide surgeons with many alternatives in a convenient arrangement. Devices that are not used are simply returned to stock for sterilization prior to a subsequent use. Non-sterile devices do not have a definitively limited shelf life, as sterile products do. Non-sterile devices are less expensive to package and sterilize. Non-sterile devices can typically be more densely packaged into a common carrier than sterile devices. The primary reason that such non-sterile products are difficult to track, however, is that the products are difficult to mark, may not be marked at all, and may be identical to other products with which they are packaged, thus creating a possibility of confusion among parts. In many instances, specific non-sterile products are not tracked beyond their manufacturing facility, and may only be counted when reconciled for payment as one of many products that were not returned to a manufacturer for replenishment.

One way of tracking non-sterile medical devices would be to encapsulate the devices in a container that includes identifying information. Such a container may advantageously provide ready access to the device by sterilizing material such as steam or other cleaning solutions. It would also be advantageous in some tracking systems for non-sterile implants to be resistant to intentional or even incidental tampering that could disassociate identifying information from a medical device.

SUMMARY

An embodiment of the invention is a medical device tracking system. The system includes a medical device and a capsule for containing the medical device. The capsule of some embodiments has a body capable of multiple fluid sterilizations without degradation, the body including openings to permit ingress and egress of fluid sterilization substances. An identification tag may also be associated with the body, and the capsule may be configured such that removal of the medical device from the capsule is thereafter detectable.

Another embodiment of the invention is a medical device tracking system that includes a medical device, a first component, a second component, and a tracking device. The first component has transverse openings along the length of the first component to permit ingress and egress of fluid sterilization substances. The second component of some embodiments is coupled with the first component to encapsulate the medical device. The tracking device may be associated with the first component or the second component.

Yet another embodiment of the invention is a steam sterilizable apparatus for containing a medical device. The apparatus may include a capsule formed in an enlarged shape of the medical device to conform to the perimeter of the medical device, and an enclosure configured to cooperate with the capsule to contain the medical device within the capsule. One or both of the capsule and the enclosure may include openings to permit steam to enter and exit the capsule to sterilize the implant.

DETAILED DESCRIPTION

Figure 1:
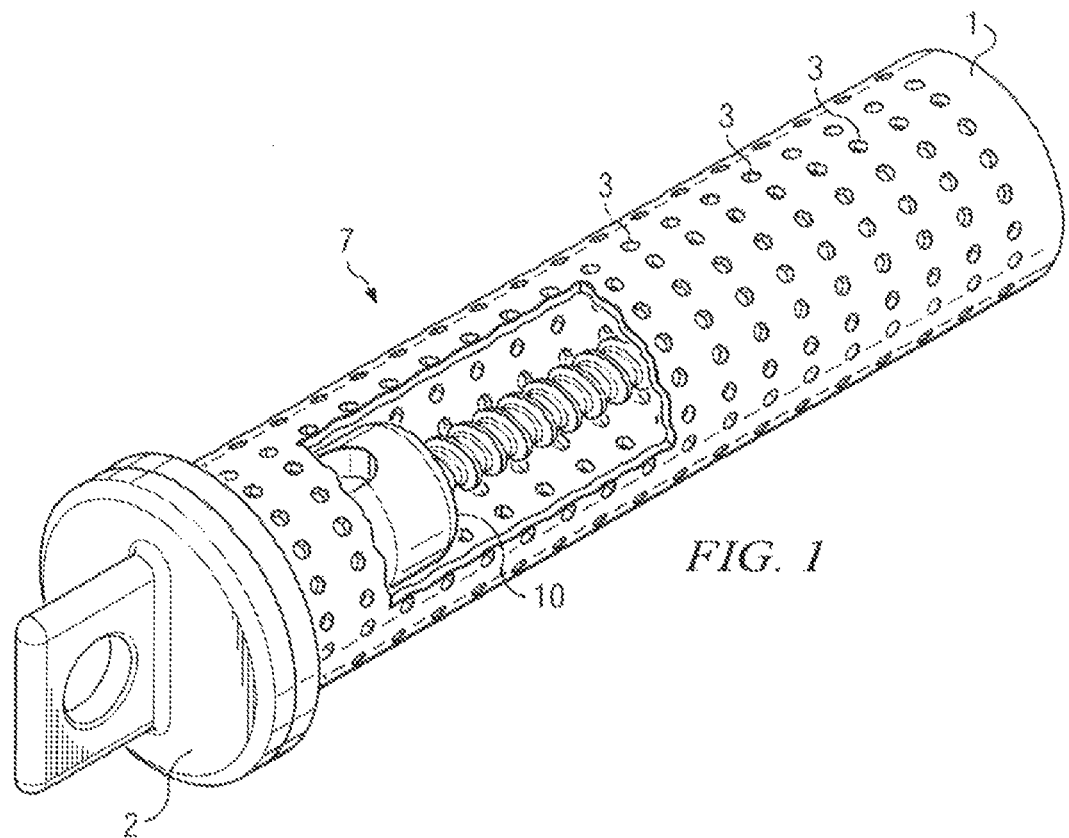
FIG. 1 is a perspective view of an embodiment of the invention that illustrates a tracking system including a spinal pedicle screw.

A medical device tracking system is illustrated in FIG. 1 that includes a medical device in the form of a spinal surgical screw 10 and a capsule 7 for containing the spinal surgical screw 10. The medical device of this or any other embodiment of the invention may be any implant or instrument used in accomplish a medical procedure. The medical device of some embodiments is capable of undergoing one or more steam sterilization cycles, or other sterilization procedures, without degrading in a manner that would make the implant unsuitable for use in a medical procedure. The medical device of this or any other embodiment of the invention may consist of materials, by way of example, and without limitation, including titanium and its alloys, ASTM material, cobalt chrome, tantalum, ceramic, poly-ether-ether-ketone (PEEK), PEAK, various plastics, plastic composites, carbon fiber composites, coral, allograft, autograft, zenograft, and can include artificial materials which are at least in part bioresorbable, or any material suitable for human implantation.

Figure 6:
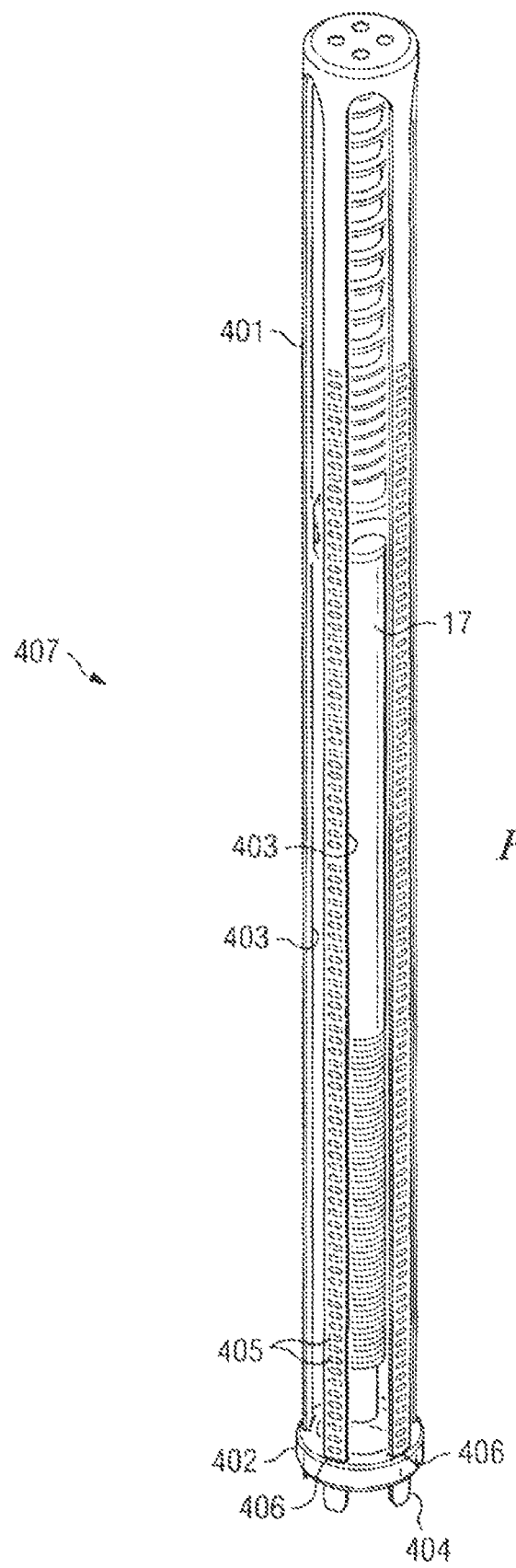
FIG. 6 is a perspective view of an embodiment of the invention that illustrates a tracking system including a spinal post.
Figure 7:
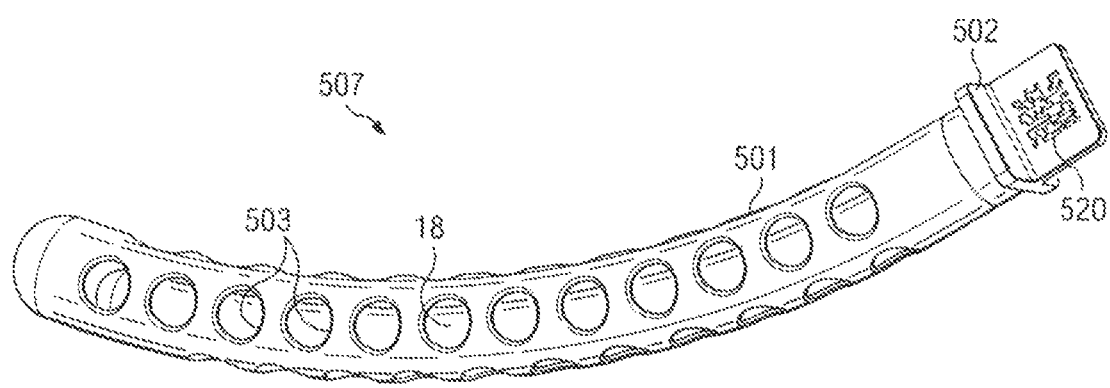
FIG. 7 is a perspective view of an embodiment of the invention that illustrates a tracking system including a spinal rod.

In addition to being a surgical screw, such as spinal surgical screw 10, the medical device may be a spinal post 17, as illustrated in FIG. 6, or a spinal rod 18, as illustrated in FIG. 7. The medical device of some embodiments may be, without limitation, a surgical screw of any variety, a spinal or other orthopedic plate, a surgical rod, an interbody spinal device, a vertebral disc arthroplasty device, a nucleus replacement device, a corpectomy device, a vertebrectomy device, a mesh device, a facet fixation or arthroplasty device, a structural bone graft, a staple, a tether of synthetic material or wire, or other spinal fixation instrumentation, an intramedullary nail, an external fixation device, a hip prosthesis or therapeutic device, a knee prosthesis or therapeutic device, or an instrument useful with any of the previously recited devices.

The capsule 7 illustrated in FIG. 1 is a body capable of multiple fluid sterilizations without degradation. For example, the capsule 7 of various embodiments may not undergo meaningful loss of structural integrity, is not discolored, or does not lose information retained on the capsule 7 as a result of multiple fluid sterilizations. The sterilizations may be from steam sterilization or from application of a chemical sterilizing substance, or from any other effective sterilization substance or process. The capsule 7 that is shown includes a first component 1 and a second component 2. The first component 1 of the illustrated embodiment has transverse openings 3 along the length of the capsule 7 to permit ingress and egress of fluid sterilization substances. In other embodiments, the second component 2 may alternatively or in addition have openings to permit passage of fluid sterilization substances.

In some embodiments, a tracking device such as an identification tag, indicia, or other marking is associated with the capsule 7. The tracking device may be more specifically associated with one or both of the first component 1 and the second component 2. The tracking device may be inscribe on a component, attached to a component, incorporated in the manufacture of a component, or in any way connected or associated with either component, a combination of the components, or provided as a supplement to the components. The tracking device may be anything that is capable of retaining identifying information. In some embodiments, the tracking device is a device suitable for scanning by an optical scanner such as a one or two dimensional bar code reader. The tracking device may also be a radio frequency identification (RFID) device that is readable through radio frequency transmission generated by an independently powered RFID device. The tracking device may be an RFID device that includes a transponder and is readable in response to a radio frequency signal transmitted to the RFID device. In some embodiments, the tracking device is a human readable visual and/or tactile device such as, but not limited to, alphanumeric characters, and may optionally include raised or lowered portions.

The capsule 7 may be configured such that removal of the spinal surgical screw 10 from the capsule 7 is thereafter detectable. As illustrated in FIG. 1 removal of the spinal surgical screw 10 from the capsule 7 may include detaching the first component 1 from the second component 2 to permit removal of the spinal surgical screw 10. The first and second components 1, 2 may be detached from one another by twisting, pulling, or otherwise creating stress in the components, or between one or both of the components. Alternatively, the first and second components 1, 2 may be detached or removed by cutting or otherwise degrading a portion of one or both of the first and second components 1, 2 or a connection between the components.

Figure 2:
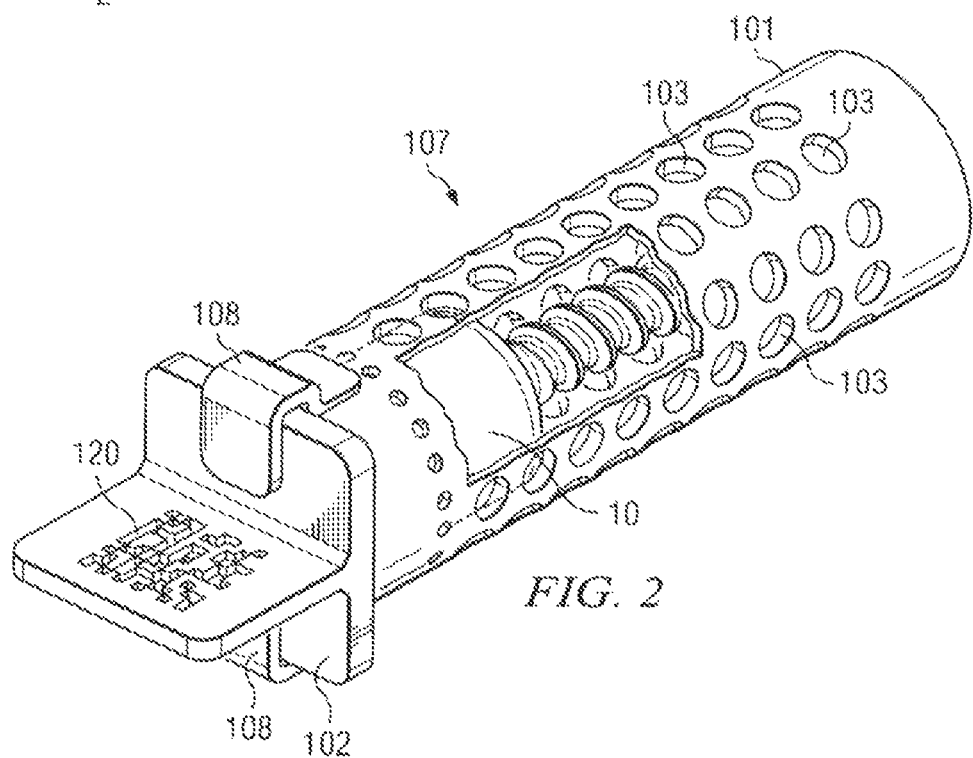
FIG. 2 is a perspective view of an embodiment of the invention that illustrates a tracking system including a spinal pedicle screw.
Figure 3:
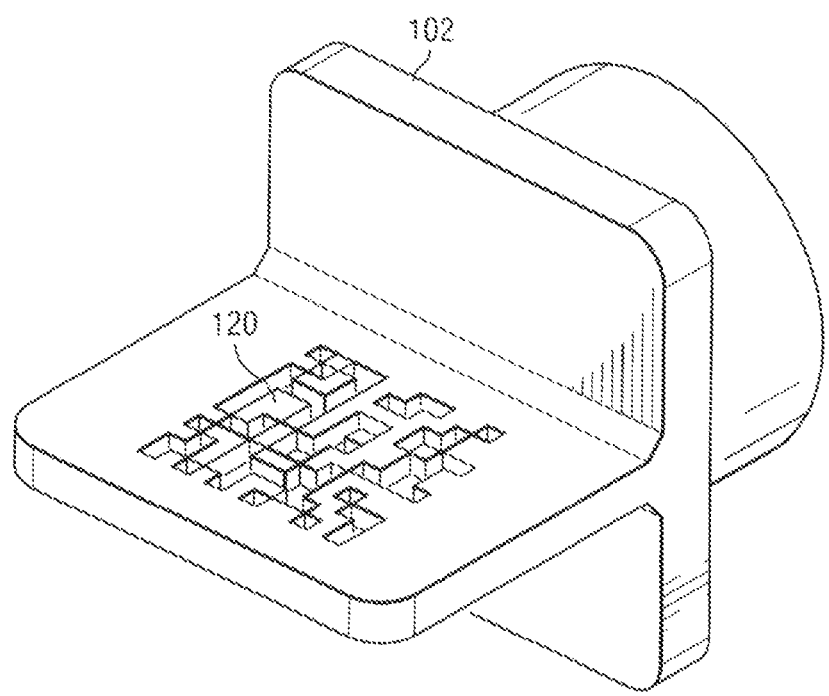
FIG. 3 is a perspective view of a component of the tracking system illustrated in FIG. 2.

FIG. 2 shows a medical device tracking system having a medical device embodied in a spinal surgical screw 10 and a capsule 107 for containing the spinal surgical screw 10. The illustrated capsule 107 is capable of multiple fluid sterilizations without degradation, and includes transverse openings 103 along the capsule 107 to permit ingress and egress of fluid sterilization substances. The capsule 107 shown comprises a first component 101 and a second component 102. A pair of connecting components 108 provides coupling mechanisms in the illustrated embodiment. A tracking device 120 may be associated with the capsule 107, and in particular with the second component 102 in the illustrated embodiment. As shown in FIGS. 2 and 3, the tracking device 120 is a two dimensional bar code marking on a side of the second component 102. A second component 102 with a tracking device 120, as illustrated in FIG. 3, may also be applicable to embodiments such as those illustrated in one or more of FIGS. 1, 2, 7, and 8. A tracking device may also be applied to the first component 101 or to one or both of the connecting components 108. In some embodiments, the capsule 107 (FIG. 2) is configured such that removal of the spinal surgical screw 10 from the capsule 107 is thereafter detectable. In addition to detection resulting from alterations in the first and second components 101, 102, detectable alterations to one or both of the connecting components 108 may result when a medical device is removed from a capsule 107.

Figure 4:
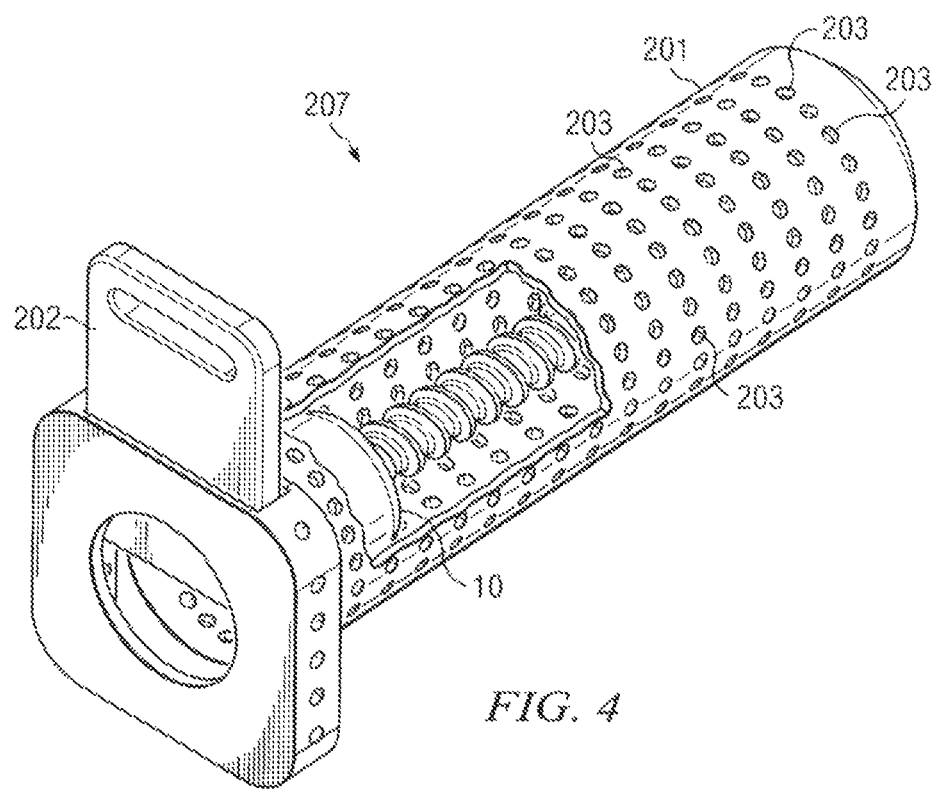
FIG. 4 is a perspective view of an embodiment of the invention that illustrates a tracking system including a spinal pedicle screw.

FIG. 4 shows a medical device tracking system having a medical device embodied in a spinal surgical screw 10 and a capsule 207 for containing the spinal surgical screw 10. The illustrated capsule 207 is capable of multiple fluid sterilizations without degradation, and includes transverse openings 203 along the capsule 207 to permit ingress and egress of fluid sterilization substances. The capsule 207 shown comprises a first component 201 and a second component 202. The second component 202 couples to the first component 201 by sliding engagement. A tracking device may be associated with the capsule 207. A tracking device may be applied to one or both of the first component 201, the second component 202, or to additional components between the components or associated with them. In some embodiments, the capsule 207 is configured such that removal of the spinal surgical screw 10 from the capsule 207 is thereafter detectable. In addition to detection resulting from alterations in the first and second components 201, 202, detectable alterations to components connecting the first and second components 201, 202 may result when a medical device is removed from a capsule 207.

Figure 5:
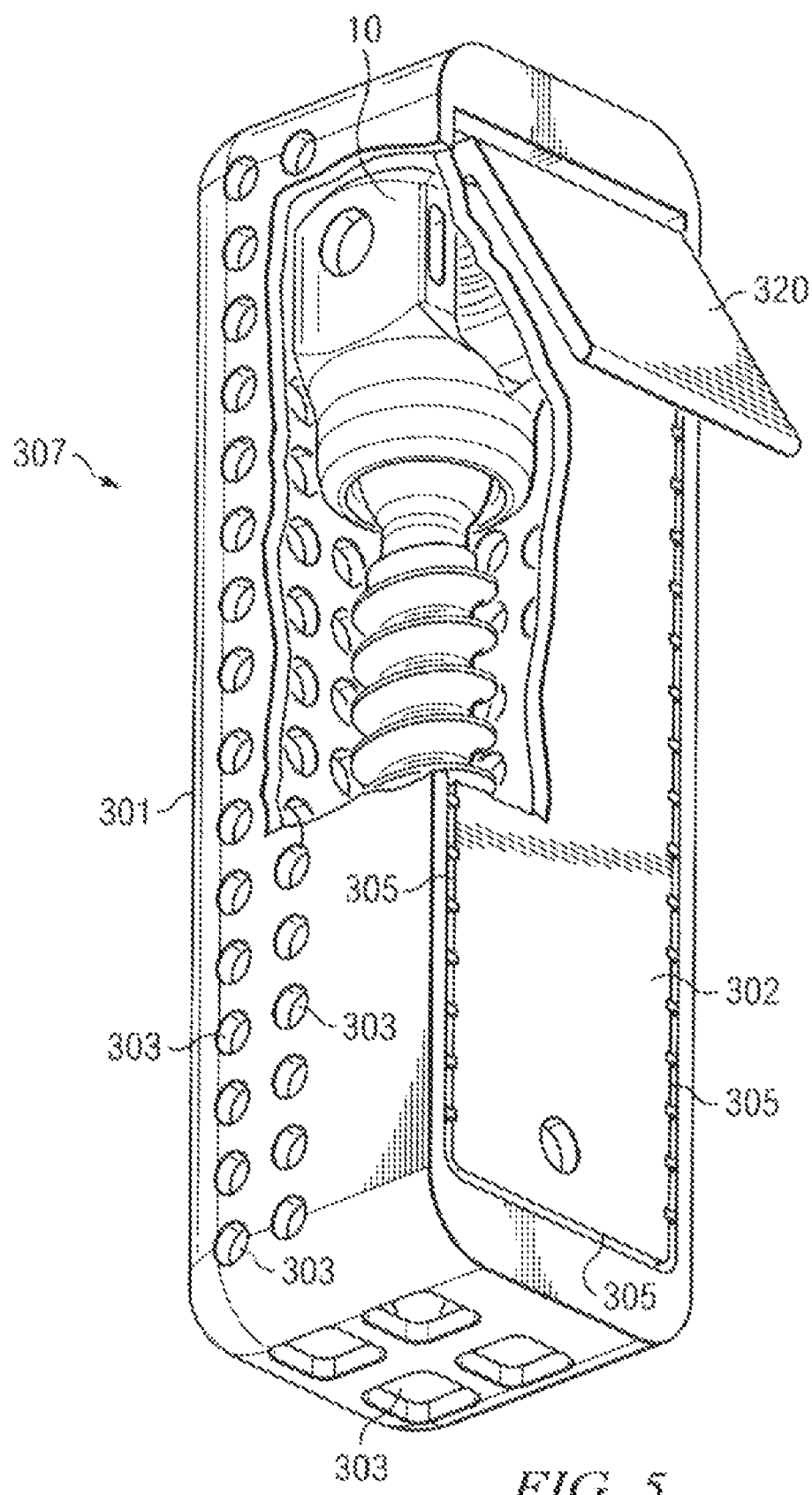
FIG. 5 is a perspective view of an embodiment of the invention that illustrates a tracking system including a spinal pedicle screw.

FIG. 5 shows a medical device tracking system having a medical device embodied in a spinal surgical screw 10 and a capsule 307 for containing the spinal surgical screw 10. The illustrated capsule 307 is capable of multiple fluid sterilizations without degradation, and includes transverse openings 303 along the capsule 307 to permit ingress and egress of fluid sterilization substances. The capsule 307 shown comprises a first component 301 and a second component 302. The second component 302 illustrated is coupled to the first component 301 along all or part of a perimeter 305 of the second component 302. A tracking device 320 may be associated with the capsule 307, and in particular with the first component 301 in the illustrated embodiment. As illustrated, the tracking device 320 may also be used as a gripping component to be grasped to pull the second component 302 away from the first component 301. A tracking device may also be applied to the first component 301. In some embodiments, the capsule 307 is configured such that removal of the spinal surgical screw 10 from the capsule 307 is thereafter detectable. In addition to detection resulting from alterations in the first and second components 301, 302, detectable alterations to the interface between the first and second components 301, 302 may result when a medical device is removed from the capsule 307.

FIG. 6 illustrates a medical device tracking system having a medical device embodied in a spinal post 17. The tracking system includes a capsule 407 for containing the spinal post 17. The illustrated capsule 407 is capable of multiple fluid sterilizations without degradation, and includes transverse openings 403 along the capsule 407 to permit ingress and egress of fluid sterilization substances. The capsule 407 shown comprises a first component 401 and a second component 402. The second component 402 illustrated is coupled to the first component 401 at a distal end 404 of the first component 401. Each of the segments of the distal end 404 of the first component 401 shown includes ratchet teeth 405 designed to interact with the second component 402 though slots 406 in the second component 402. In an embodiment of the system, the ratchet teeth 405 only permit the second component to slide proximally along the first component 401. Consequently, the spinal post 17 is captured between the first component 401 and the second component 402 as the second component is advanced proximally along the first component 401. A tracking device may be associated with the capsule 407 or particularly one of its components. In some embodiments, the capsule 407 is configured such that removal of the spinal post 17 from the capsule 407 is thereafter detectable. In addition to detection resulting from alterations in the first and second components 401, 402, detectable alterations to the interface between the first and second components 401, 402 may result when a medical device is removed from the capsule 407.

FIG. 7 illustrates a medical device tracking system having a medical device embodied in a spinal rod 18. The tracking system includes a capsule 507 for containing the spinal rod 18. The illustrated capsule 507 is capable of multiple fluid sterilizations without degradation, and includes transverse openings 503 along the capsule 507 to permit ingress and egress of fluid sterilization substances. The capsule 507 shown comprises a first component 501 and a second component 502. A tracking device may be associated with the capsule 507 or particularly one of its components. As illustrated, a tracking device 520 comprising a two dimensional bar code is a part of the second component 502. In some embodiments, the capsule 507 is configured such that removal of the spinal rod 18 from the capsule 507 is thereafter detectable. In addition to detection resulting from alterations in the first and second components 501, 502, detectable alterations to the interface between the first and second components 501, 502 may result when a medical device is removed from the capsule 507.

In another aspect, FIG. 7 illustrates the capsule 507 as a steam sterilizable apparatus for containing a medical device such as the spinal rod 18. The capsule 507 shown is formed in an enlarged shape of the spinal rod 18. In some embodiments, this enlarged shape enables steam or other sterilization substances to access the surface of a contained medical device, while not taking up any more volume than is necessary to access the surfaces of the medical device. The common, although enlarged, shape may also be useful to enable quickly identifying a medical device. Enlarged shapes of the invention may conform to the perimeter of the medical device. As used herein, the perimeter may include precisely the outer boundaries of a medical device, or may more generally include various approximations of the outer boundaries of a medical device. A capsule 507 of an embodiment includes a first component 501 and a closure, for example in the form of the second component 502. The closure of some embodiments may also be incorporated into a single component that makes up a capsule. As illustrated, the capsule 507 includes openings 503 to permit steam to enter and exit the capsule 507 to sterilize the spinal rod 18. In other embodiment, the second component 502, or other parts of the first component 501, may include openings to permit steam to enter and exit.

The coupling between the first and second components 1, 2; 101, 102; 201, 202; 301, 302; 401, 402; 501, 502 of some embodiments is such that once the components are coupled together, then separation of the components is detectable. This may be accomplished, without limitation, by applying adhesive between the components, by providing ratcheting or snap-fit connections designed to fracture relatively easily as compared to other portions of the mechanism when stressed, by melting, welding, or otherwise joining all or a portion of the components together, and by including a indicator device across a joint between or through the components that fracture, change shape, change color, or otherwise are altered by separation of the first and second components. Detectable separation of the components may occur at one or more connections between the components, or may include fracture or change within either or both of the first and second components. In some embodiments, the first and second components, and in some instances other components, form a mechanism configured such that removal of the medical device from the mechanism is detectable as specifically described, or in another manner.

Figure 8:
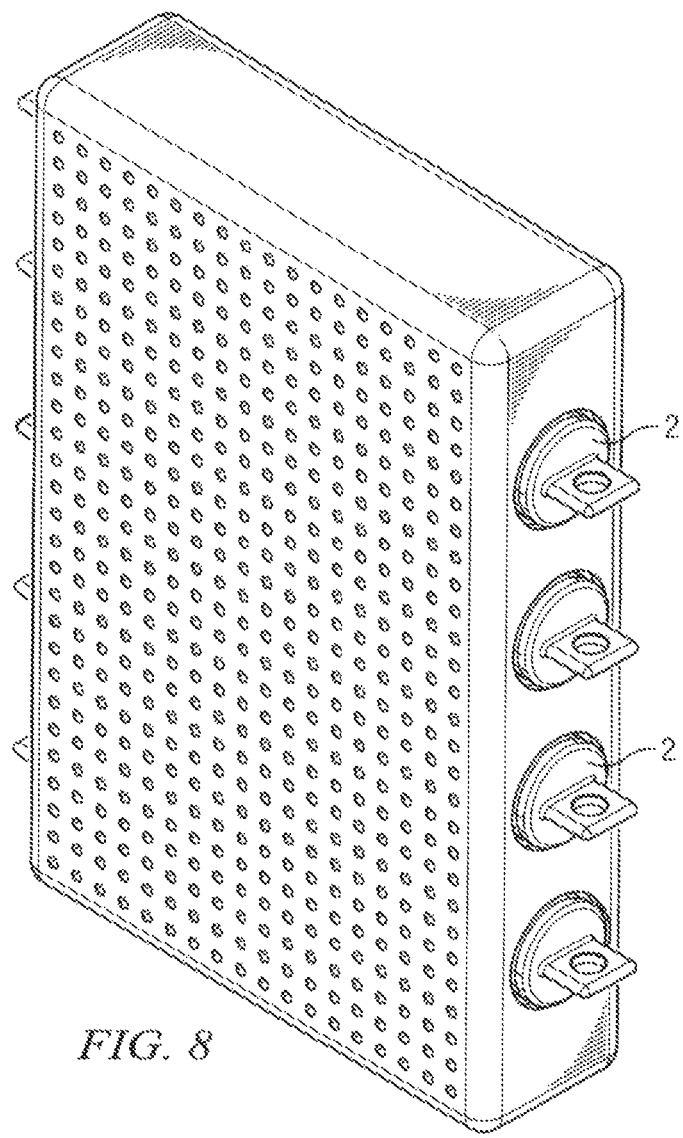
FIG. 8 is a perspective view of an embodiment of the invention that illustrates a tracking system including multiple capsules coupled to form an array.

FIG. 8 illustrates a system that may be essentially similar to the system described for FIG. 1, but additionally includes other capsules coupled with the capsule 7 described in association with FIG. 1. Each additional capsule is configured to receive one or more additional medical devices, such as, for example, spinal surgical screws 10. The additional capsules may be formed in a common material piece as illustrated, or may be formed in multiple material pieces and bound together subsequently. One or more of the capsule and additional capsules may be configured such that removal of a respective medical device is thereafter detectable, as described in connection with any of the embodiments herein.

Figure 9:
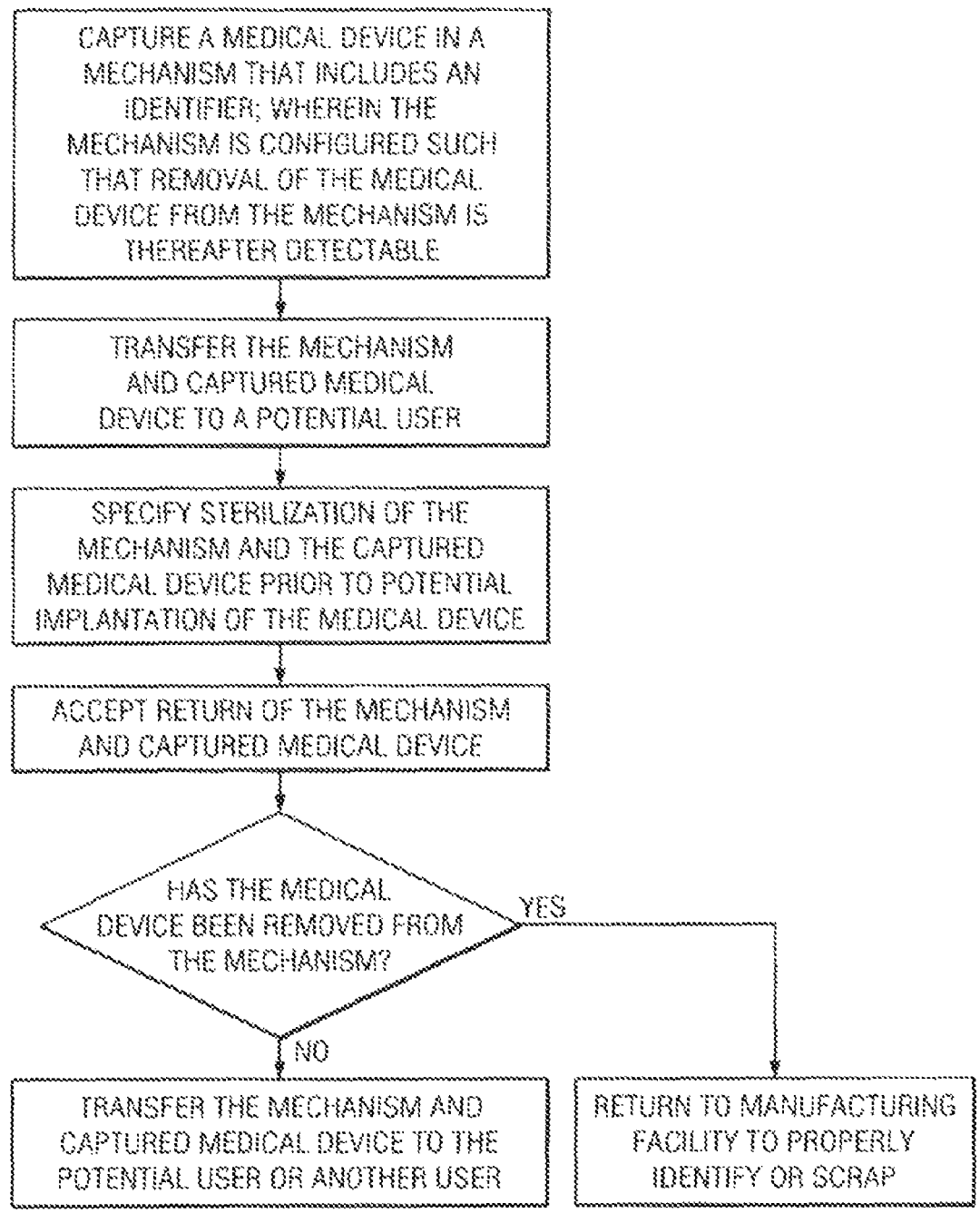
FIG. 9 is a flowchart directed to method embodiments of the invention.

FIG. 9 graphically illustrates a method of tracking a medical device. The method includes capturing the medical device in a mechanism that includes an identifier, wherein the mechanism is configured such that removal of the medical device from the mechanism is thereafter detectable. The medical device captured may be similar to any of the medical devices illustrated in FIGS. 1, 2, and 4-8, any medical device otherwise described herein, or any medical device suitable to receive an identifier.

The method of some embodiments also includes transferring the mechanism and captured medical device to a potential user. A mechanism and medical device may be transferred to a user who has purchased the medical device, who has accepted the medical device on consignment, who is receiving the medical device on loan, or who is otherwise in authorized possession of the medical device. A user under various embodiments of the invention may be a specific physician, a group of physicians, a hospital, a clinic, a governmental agency, or any person or group administering receipt of medical devices. The method may further include specifying sterilization of the captured medical device prior to potential implantation of the medical device. The form of sterilization may be particularly specified, or may be left to the discretion of the user.

Method embodiments may also include accepting return of the mechanism and captured medical device. The original manufacturer or provider of the medical device would typically accept return. However, as understood herein, accepting return may also include return being accepted by an agent or otherwise authorized party acting on behalf of the original manufacturer or provider of the medical device. In some, but not all instances, return of medical devices is a result of a provider sending multiple sizes and/or configurations of a medical device to a user with an understanding that not all of the medical devices will be employed in a planned procedure.

As shown in FIG. 9, some embodiments of the invention further include checking one or both of the medical device and the mechanism to determine if the medical device has been removed from the mechanism. Such a check may include one or more of determining if the mechanism is currently present and determining if the mechanism has been previously removed from the medical device. If the medical device has been removed from the mechanism, the medical device may be returned to a manufacturing or processing facility to be identified properly, or scrapped if tracking has been lost for the device. If the medical device has not been removed from the mechanism, a method under the invention may include subsequently transferring a previously delivered and returned mechanism and captured medical device to a previous potential user or to a new user. The term new user as used herein may also refer to a new potential user. The step of checking the medical device and mechanism for removal may occur at different or additional times in some other embodiments of the invention in order to verify continued, accurate tracking of a medical device.

Some embodiments of the invention may also include maintaining a record of the identifier, and therefore, maintaining a record of the medical device that has been associated with the identifier and the mechanism in which the identifier is embodied. Consequently, by maintaining a record of the identifier, information associated with the medical device may be effectively maintained. The types of information that may be maintained in certain embodiments include the location of the identifier and medical device at a particular time, the patient or patients in or on whom a medical device has been used, and the healthcare provider or providers who have used or handled a device. A healthcare provider may include physicians, nurses, technicians, hospitals, purchasing agents, governmental agencies, administrative staff, and others. Tracked information associated with a medical device may also include a date of use, a time of use, a condition treated, a particular surgical procedure, a procedure type, a number of times sterilized, and other information that might be useful in tracking the safety, utility, and efficacy of a medical device. An identifier and medical device may also be associated in some embodiments with manufacturing information, such as but not limited to, material type, lot number, country where manufactured, manufacturing facility, time of manufacture, and manufacturing process employed.

In any of the embodiments of the present invention, the medical devices may include, be made of, treated, coated, filled, used in combination with, or have a hollow space or opening for containing artificial or naturally occurring materials and/or substances suitable for implantation in the human body. These materials, and/or substances, may include any source of osteogenesis, bone growth promoting materials, bone derived substances or products, demineralized bone matrix, mineralizing proteins, ossifying proteins, bone morphogenetic proteins, hydroxyapatite, genes coding for the production of bone, and bone including, but not limited to, cortical bone, antibiotics, cancer treating substances, infection treating substances, substances to therapeutically affect clotting or stenosis, or other disease treating substances. The medical devices can include, at least in part materials that are bioabsorbable and/or resorbable in the body.

While the invention has been described with reference to particular embodiments, it will be appreciated by those of ordinary skill in the art that various modifications can be made to the invention itself without departing from the spirit and scope thereof. All changes and modifications that are within the spirit of the invention are hereby anticipated and claimed.

What is claimed is:

1. A steam sterilizable apparatus for containing a medical device comprising:
   a capsule formed in an enlarged shape of the medical device to conform to the perimeter of the medical device; and
   an enclosure configured to cooperate with the capsule to contain the medical device within the capsule;
   wherein one or both of the capsule and the enclosure include at least two transverse openings to permit steam to enter and exit the capsule to sterilize the implant.

2. The apparatus of claim 1 further comprising a medical device.

3. A sterilizable apparatus for containing a medical device comprising:
   a capsule for containing the medical device, wherein the capsule includes a body having a first end and a second end and a length between the first end and the; second end the body having at least two substantially transverse openings along the length to permit ingress and egress of a fluid sterilization substance, and wherein the capsule is configured such that removal of the medical device from the capsule is detectable.

4. The sterilizable apparatus according to claim 3 wherein the length is along a greater dimension of the body.

5. The sterilizable apparatus according to claim 3 further comprising a tracking device associated with the body.

6. The sterilizable apparatus according to claim 5 wherein the tracking device is suitable for scanning by an optical scanner.

7. The sterilizable scramble apparatus according to claim 5 wherein the tracking device is readable through radio frequency transmission.

8. The sterilizable apparatus according to claim 7 wherein the tracking device is a radio frequency identification device (RFID) that includes a transponder.

9. The sterilizable apparatus according to claim 3 wherein the fluid sterilization substance is steam sterilization.

10. The sterilizable apparatus according to claim 3 wherein removal of the medical device from the capsule is detectable at least in part by non-resilient deformation of the capsule.

11. A sterilizable apparatus for containing a medical device comprising:

a capsule for containing the medical device, wherein the capsule includes a body having a first end and a second end, a length along a greater dimension of the body between the first end and the second end, the body having at least two substantially transverse openings along the length to permit ingress and egress of a fluid sterilization substance, and wherein the capsule is configured such that the medical device can be removed from the capsule.

12. The sterilizable apparatus according to claim 11 further comprising a tracking device associated with the body.

* * * * *